United States Patent [19]

Baum et al.

[11] Patent Number: 5,371,332
[45] Date of Patent: Dec. 6, 1994

[54] SENSOR CONTROL AND DISPLAY UNIT FOR DENTAL APPARATUS

[75] Inventors: Marcus Baum, Bensheim; Markus Born, Ehringshausen; Guenther Moritz, Lampertheim; Klaus Stoeckl, Bensheim, all of Germany

[73] Assignee: Siemens Aktiengesellschaft, Munich, Germany

[21] Appl. No.: 9,119

[22] Filed: Jan. 26, 1993

[30] Foreign Application Priority Data

Jan. 29, 1992 [DE] Germany .................. 4202438

[51] Int. Cl.⁵ .............. H01H 13/70; A61C 19/00
[52] U.S. Cl. .................. 200/5 A; 433/229
[58] Field of Search .......... 200/5 A, 512–517, 200/600, 310–317; A61C 1/00, 19/00; H01H 13/70, 9/18

[56] References Cited

U.S. PATENT DOCUMENTS

| | | | |
|---|---|---|---|
| 3,699,294 | 10/1972 | Sudduth | 200/5 A |
| 4,382,165 | 5/1983 | Balash et al. | 200/5 A |
| 4,594,482 | 6/1986 | Saito et al. | 200/5 A |
| 4,644,326 | 2/1987 | Villalobos et al. | 341/34 |
| 4,646,062 | 2/1987 | Arakawa | 200/514 X |
| 4,746,953 | 5/1988 | Knodt | 200/5 A X |
| 4,894,493 | 1/1990 | Smith et al. | 200/5 A |
| 4,901,074 | 2/1990 | Sinn et al. | 200/5 A X |
| 5,033,238 | 7/1991 | Zubler | 51/165.74 |
| 5,084,730 | 1/1992 | Deguchi | 355/75 |

FOREIGN PATENT DOCUMENTS

| | | | |
|---|---|---|---|
| 0366832 | 5/1990 | European Pat. Off. | H01H 13/70 |
| 3717325 | 11/1987 | Germany | H01H 9/18 |
| WO89/05613 | 6/1989 | WIPO | A61C 19/00 |

Primary Examiner—J. R. Scott
Attorney, Agent, or Firm—Hill, Steadman & Simpson

[57] ABSTRACT

A control board for a dental apparatus contains a control panel (1) having a plurality of key surfaces (2) for the actuation of sensor devices (3) that respond to a force or a change in force. The sensor devices (3), facing toward the operating side, are covered by a thin front plate (4a) of transparent material. The front plate (4a) is provided with an all around, lateral edge (5) that is an integral component part of the front plate (4a) and thus forms a frame (4) that is closed at the front side and surrounds the control panel. At least the front plate (4a) and, preferably, the entire frame (4) is composed of glass.

20 Claims, 2 Drawing Sheets

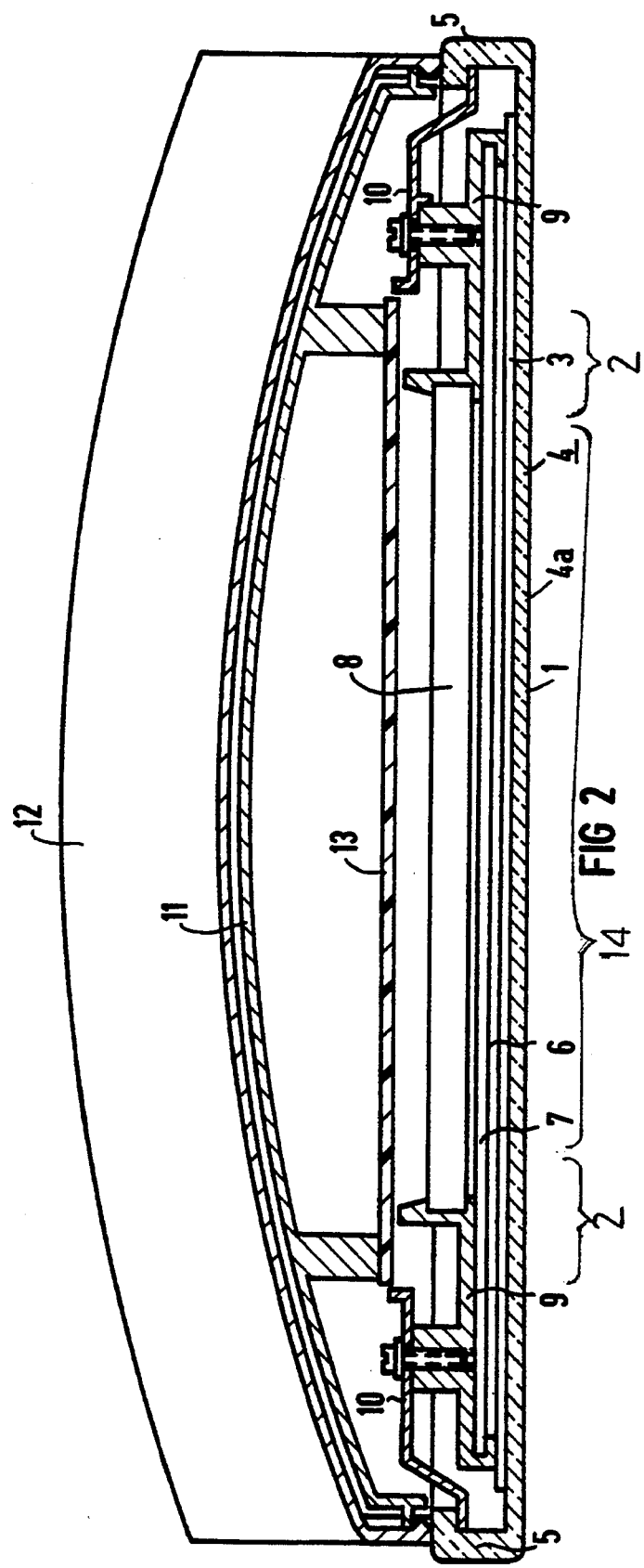

SENSOR CONTROL AND DISPLAY UNIT FOR DENTAL APPARATUS

BACKGROUND OF THE INVENTION

The present invention is directed to a control board for a dental apparatus that contains a control panel having a plurality of key surfaces for the actuation of sensor means that respond to a force or change in force.

In prior art control boards of this type, the control panels are predominantly executed in foil technique wherein foil keyboards are positioned on a carrier surface or are also glued behind a frame. For example, a control panel of this type is known from the Company Brochure "KaVo-SYSTEMATICA 1062" No. WTE-PR-NO. 829712 VI 91 of Kaltenbach & Voigt, Biberach. In such an arrangement an edge gap always occurs in which dirt and moisture can collect. Added thereto is that cleaning and disinfection of the surface is relatively difficult to carry out. A further disadvantage is that the foil keyboard can be relatively easily damaged.

European reference EP-A1-0 366 832 discloses a rigid plate of metal (aluminum or brass) or wood arranged over a foil keyboard in order to protect it. The rigid plate is so thick that the foil keyboard lying therebelow cannot be faultlessly actuated given pressure on the plate, whether it is because no key responds or because a plurality of keys simultaneously respond. In order to be able to actuate the keyboard, it is proposed in this reference to provide zones of reduced stiffness in the plate, namely over the respective key regions of the foil keyboard. The zones of reduced thickness can be created by changes in the material properties of the plate at the respective location. Alternatively, recesses can be provided at the corresponding locations, these being open toward the foils and being selected of such a depth that the plate part remaining over the recess has adequate elasticity in order to relay the finger pressure for key actuation onto the key.

U.S. Pat. No. 4,382,165 discloses a keyboard wherein two interconnects containing the switch elements are arranged sandwich-like between two rigid plates.

German reference DE-C2-3 717 325 discloses a transparent, touch-sensitive control panel that has a transparent, touch-sensitive contact region with a plurality of individual contacts arranged in a two-dimensional grid. The contact area is composed of an upper plate of transparent plastic film, a lower plate of a similar, transparent material and an insulating spacer situated therebetween. The contact arrangement is mounted on a base plate that is also composed of transparent plastic.

The principal aim of this control panel is to prevent foreign material being introduced into or enclosed in the light path, in order to assure that the image of the visual display that is seen through the touch-sensitive switch is neither distorted nor interrupted. Further, the formation of Newtonian rings that would form as a result of the air layer between the lower plate and the base plate is to be prevented.

SUMMARY OF THE INVENTION

It is an object of the present invention to provide a control board for a dental apparatus wherein the control panel meets the current hygiene requirements in the medical field. In particular, the control panel should not have any edge gaps in which dirt and moisture can collect and in which germs can multiply as a result thereof. Furthermore, the control panel should be optimally cleanable and disinfectable.

An optimum cleaning and disinfection is established, in particular, in that the front plate is provided with an all around, lateral edge and the edge is an integral component part of the front plate, thus forming a frame closed at the front that surrounds the control panel. The frame can be easily secured to a carrier and has no edge gaps whatsoever. What are referred to as pressure and position sensors according to FPSR (force and position sensor resisting) technology are advantageously utilized; alternatively, piezo sensors are utilized. The front plate is advantageously composed of glass, as a result whereof the sensor means are protected both from mechanical damage, as well as, from the damaging influences of chemical materials used in a dental practice.

In general terms the present invention is a control board for a dental apparatus, containing a control panel having a plurality of key surfaces for actuation of sensor means that respond to a force or a change in force. The sensor means, facing toward an operating side, are covered by a thin front plate of transparent material. The front plate is provided with an all around, lateral edge that is an integral component part of the front plate and thus forms a front frame closed at the front side which surrounds the control panel.

Advantageous developments of the present invention are as follows.

The edge is fashioned as one piece. The edge, the front plate and/or the entire frame is composed of glass.

The sensor means are arranged sandwich-like between the front plate and a seating plate, and a display unit presses against the seating plate. Alternatively, the sensor means are arranged sandwich-like between the front plate and the display unit, whereby the display unit presses planarly against the sensor means. The display unit is a liquid crystal display.

The edge is fashioned such that it accepts retainer elements that interact with an assembly and adjustment frame that presses the display unit against the seating plate.

A carrier is provided that has a front side to which an assembly unit is secured which contains the assembly and adjustment frame, the front plate, the sensor means, the seating plate, the display unit and an illumination means, and a back side to which a cover is secured.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures in which like reference numerals identify like elements, and in which:

FIG. 2 depicts the control board in cross section along the line II—II in FIG. 1.

DESCRIPTION OF THE PREFERRED EMBODIMENT

Figure 1:
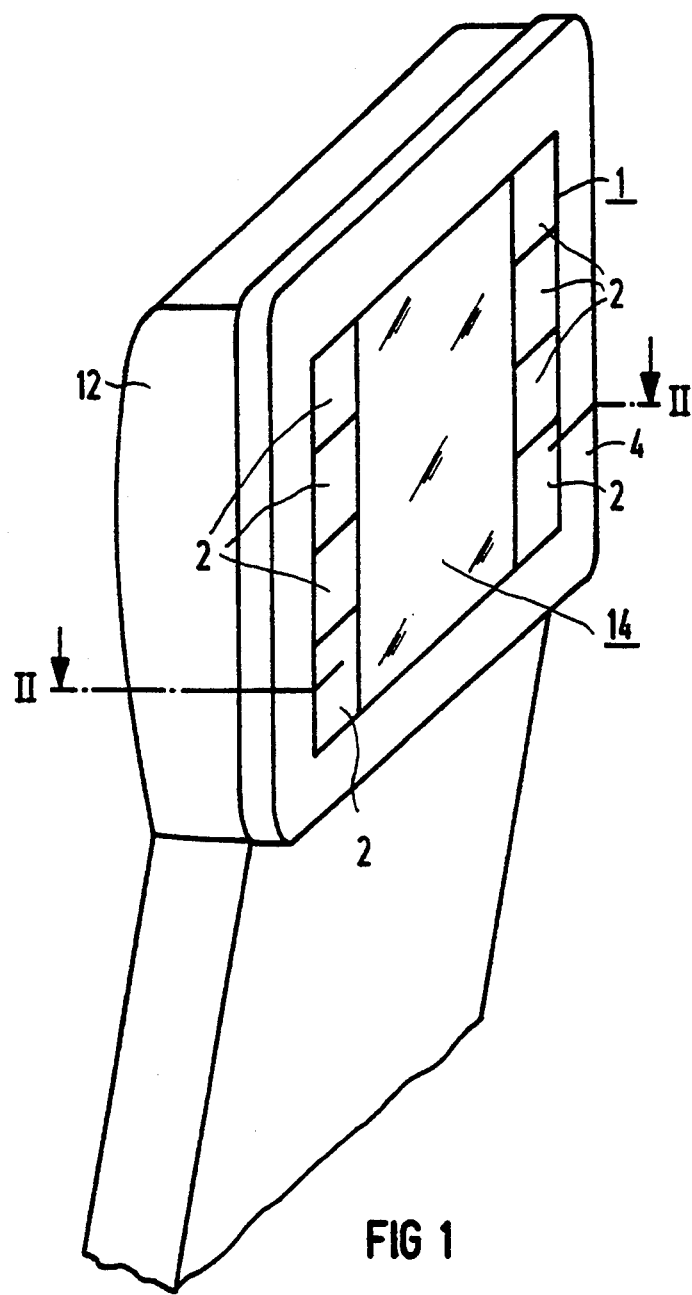
FIG. 1 is a perspective view of a control board for a dental apparatus.

The control board of the present invention is allocated to dental equipment (not shown in the drawing) and is intended, for example, to be able to select and trigger specific chair and/or apparatus functions. The control board contains a control panel 1 having a plurality of key surfaces 2 arranged at both sides to which sensor means 3 of the type initially cited is allocated. Since the sensor means 3 is not the subject matter of the present invention (but is of a known, commercially available type, for example, piezo elements), the structure of this sensor means is not shown in detail in FIG. 1. Facing toward an operating side, the sensor means 3 is covered by the front plate 4a of a glass frame 4. The front plate 4a is planar and has a thickness of approximately 1–2 mm. The front plate 4a merges into an all around, lateral edge 5. This edge 5 is an integral component part of the glass frame 4. The glass frame is fashioned as one piece in the illustrated embodiment. However, it is within the framework of the present invention to execute the glass frame in multi-part fashion and to join the individual parts to one another in a suitable manner, for example, by gluing.

The sensor means 3 is arranged sandwich-like between the front plate 4a of the glass frame 4 and a seating plate 6. Advantageously, the sensor means 3 is glued to the seating plate 6 and to the glass frame 4. As a result thereof, unwanted gaps between the glass frame and the sensor means are avoided and malfunctions are largely suppressed. For stability reasons, the seating plate 6 is approximately 1–2 mm thick. A display unit 7 in the form of a LCD (liquid crystal display), that presses planarly against the seating plate 6 with a slight prestress, is located behind the seating plate. The thickness of the seating plate can be reduced with this arrangement. Alternatively to this arrangement, the display unit 7 can planarly press directly against the sensor means 3 and the seating plate 6 can be eliminated. Seating plate 6 and display unit 7 together with an illumination unit 8 are secured to a mounting and adjustment frame 9. The latter in turn is secured to the glass frame 4 with retainer and catch elements 10 such that a compact assembly unit results. In a way not visible here, for example by screwing to the part 9, this assembly unit is held to a carrier 11 at whose back side a cover 12 is put in place in a snap-in technique and to the front side whereof a motherboard 13 is secured for accepting the required drive electronics for the sensor means as well as for the illumination.

Alternatively to the piezo elements responding to a change in force that have been set forth, elements that respond to force, for example elements according to the afore-mentioned FPSR technology, can also be provided. In conclusion, let it be pointed out that the glass frame need be transparent only in the region of a display (referenced 14 in FIG. 1).

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. A control and display board for a dental apparatus, comprising:
    a control panel having a thin front plate of transparent material, said front plate having a substantially central information display area and a plurality of key surfaces in a further area that is laterally adjacent to said information display area;
    sensor means actuated via said key surfaces, said sensor means responding to a force or a change in force and said sensor means being covered by respective key surfaces of said front plate;
    a display unit arranged at least behind said central information display area of said front plate; and
    the front plate having the all around lateral edge that is an integral component part of the front plate and that extends out of a plane of the front plate, the front plate and the all around lateral edge forming a front frame closed at a front side thereof which surrounds the control panel.

2. The control board according to claim 1, wherein the all around edge lateral is one piece.

3. The control board according to claim 1, wherein the control board further comprises a seating plate and wherein sensor means are arranged sandwich-like between the front plate and the seating plate, and wherein the display unit presses against the seating plate.

4. The control board according to claim 3, wherein the display unit is a liquid crystal display.

5. A control board for a dental apparatus, the control board having a control panel having a plurality of key surfaces for actuation of sensor means that respond to a force or a change in force, comprising:
    a thin front plate of transparent material covering the sensor means that face toward an operating side of the control board, the key surfaces being an integral part of the front plate;
    the front plate having the all around lateral edge that is an integral component part of the front plate and that extends out of a plane of the front plate, the front plate and the all around lateral edge forming a front frame closed at a front side thereof which surrounds the control panel;
    an assembly and adjustment frame, and retainer elements for attaching the all around lateral edge to the assembly and adjustment frame to thereby press the display unit against the seating plate.

6. The control board according to claim 5, wherein the control board further comprises an illumination means secured to the assembly and adjustment frame adjacent the display unit, and wherein the control board further comprises an assembly unit that contains the assembly and adjustment frame, the front plate, the sensor means, the seating plate, the display unit and the illumination means, and wherein the control board further comprises a carrier to which is secured the assembly unit on a front side of the carrier and a cover on a back side of the carrier.

7. The control board according to claim 1, wherein the sensor means are arranged sandwich-like between the front plate and the display unit, and wherein the display unit presses planarly against the sensor means.

8. The control board according to claim 7, wherein the display unit is a liquid crystal display.

9. The control board according to claim 1, wherein at east the front plate is composed of glass.

10. The control board according to claim 1, wherein the entire front frame is composed of glass.

11. A control and display board for a dental apparatus, comprising:
    a control panel having a glass front plate, said front plate having a substantially central information display area and a plurality of key surfaces in a further area that is laterally adjacent to said information display area;

sensor means actuated via said key surfaces, said sensor means responding to a force or a change in force and said sensor means being covered by respective key surfaces of said front plate;

a display unit arranged at least behind said central information display area of said front plate; and the front plate having a one piece glass all around lateral edge that is an integral component part of the front plate and that extends out of a plane of the front plate, the front plate and the all around lateral edge forming a front frame closed at a front side thereof which surrounds the control panel.

12. The control board according to claim 11, wherein the control board further comprises a seating plate and wherein sensor means are arranged sandwich-like between the front plate and the seating plate, and wherein the display unit presses against the seating plate.

13. The control board according to claim 12, wherein the display unit is a liquid crystal display.

14. The control board according to claim 12, wherein the control board further comprises an assembly and adjustment frame, and retainer elements for attaching the all around lateral edge to the assembly and adjustment frame to thereby press the display unit against the seating plate.

15. The control board according to claim 5, wherein the control board further comprises an illumination means secured to the assembly and adjustment frame adjacent the display unit, and wherein the control board further comprises an assembly unit that contains the assembly and adjustment frame, the front plate, the sensor means, the seating plate, the display unit and the illumination means, and wherein the control board further comprises a carrier to which is secured the assembly unit on a front side of the carrier and a cover on a back side of the carrier.

16. The control board according to claim 11, wherein the sensor means are arranged sandwich-like between the front plate and the display unit, and wherein the display unit presses planarly against the sensor means.

17. The control board according to claim 16, wherein the display unit is a liquid crystal display.

18. A control board for a dental apparatus, the control board having a control panel having a plurality of key surfaces for actuation of sensor means that respond to a force or a change in force, comprising:

a glass front plate covering the sensor means that face toward an operating side of the control board, the key surfaces being an integral part of the front plate;

the front plate having a one piece glass all around lateral edge that is an integral component part of the front plate and that extends out of a plane of the front plate, the front plate and the all around lateral edge forming a front frame closed at a front side which surrounds the control panel;

a seating plate and a display unit, sensor means being arranged sandwich-like between the front plate and the seating plate and the display unit pressing against the seating plate; and an assembly and adjustment frame, and retainer elements for attaching the all around lateral edge to the assembly and adjustment frame to thereby press the display unit against the seating plate.

19. The control board according to claim 18, wherein the display unit is a liquid crystal display.

20. The control board according to claim 18, wherein the control board further comprises an illumination means secured to the assembly and adjustment frame adjacent the display unit, and wherein the control board further comprises an assembly unit that is composed of at least the assembly and adjustment frame, the front plate, the sensor means, the seating plate, the display unit and the illumination means, and wherein the control board further comprises a carrier to which is secured the assembly unit on a front side of the carrier and a cover on a back side of the carrier.

* * * * *